US012582615B2

(12) United States Patent
Das et al.

(10) Patent No.: US 12,582,615 B2
(45) Date of Patent: ***Mar. 24, 2026

(54) TOPICAL ANALGESIC GEL COMPOSITIONS

(71) Applicant: Bayer HealthCare LLC, Indianola, PA (US)

(72) Inventors: Debanjan Das, Morristown, NJ (US); Emanuel Vizzotti, Millburn, NJ (US); Thomas Dann, Palm Harbor, FL (US); Renee Nelson, Brandon, FL (US); Courtney C. Haynes, Dunedin, FL (US); Soundarya Vaithianathan, Parsippany, NJ (US); Reginald Bradley, Bedminster, NJ (US); Reinhard Walter, Morristown, NJ (US); Gerard Meisel, Budd Lake, NJ (US)

(73) Assignee: Bayer HealthCare LLC, Indianola, PA (US)

( * ) Notice: Subject to any disclaimer, the term of this patent is extended or adjusted under 35 U.S.C. 154(b) by 54 days.

This patent is subject to a terminal disclaimer.

(21) Appl. No.: 18/118,212

(22) Filed: Mar. 7, 2023

(65) Prior Publication Data

US 2023/0285320 A1 Sep. 14, 2023

Related U.S. Application Data

(63) Continuation of application No. 16/856,176, filed on Apr. 23, 2020, now Pat. No. 11,617,727.

(60) Provisional application No. 62/841,103, filed on Apr. 30, 2019.

(51) Int. Cl.

| | |
|---|---|
| *A61K 31/125* | (2006.01) |
| *A61K 9/00* | (2006.01) |
| *A61K 9/06* | (2006.01) |
| *A61K 31/045* | (2006.01) |
| *A61K 47/10* | (2017.01) |
| *A61K 47/44* | (2017.01) |

(52) U.S. Cl.
CPC .......... *A61K 31/125* (2013.01); *A61K 9/0014* (2013.01); *A61K 9/06* (2013.01); *A61K 31/045* (2013.01); *A61K 47/10* (2013.01); *A61K 47/44* (2013.01)

(58) Field of Classification Search
CPC .. A61K 31/125; A61K 31/045; A61K 9/0014; A61K 9/06; A61K 47/10; A61K 47/44
See application file for complete search history.

(56) References Cited

U.S. PATENT DOCUMENTS

| | | | |
|---|---|---|---|
| 4,316,887 A * | 2/1982 | Kamishita | A61K 31/125 514/724 |
| 5,124,320 A | 6/1992 | Ivy et al. | |
| 5,725,874 A | 3/1998 | Oda et al. | |
| 6,133,327 A | 10/2000 | Kimura et al. | |
| 6,328,982 B1 | 12/2001 | Shiroyama et al. | |
| 6,350,785 B2 | 2/2002 | Gehlsen | |
| 6,471,944 B1 | 10/2002 | Uchiyama et al. | |
| 6,524,594 B1 | 2/2003 | Santora et al. | |
| 6,653,352 B2 | 11/2003 | Barr et al. | |
| 6,730,288 B1 | 5/2004 | Abram | |
| 6,780,443 B1 | 8/2004 | Nakatsu et al. | |
| 6,890,567 B2 | 5/2005 | Nakatsu et al. | |
| 6,899,901 B2 | 5/2005 | Nakatsu et al. | |
| 7,781,429 B2 * | 8/2010 | Schwarz | A61K 31/00 514/412 |
| 7,820,177 B2 | 10/2010 | Kruse et al. | |
| 7,829,099 B2 | 11/2010 | Woeller et al. | |
| 8,039,011 B2 | 10/2011 | Flugge-berendes et al. | |
| 8,496,950 B2 | 7/2013 | Sorge et al. | |
| 8,568,795 B2 | 10/2013 | Sigurjonsson et al. | |
| 8,685,381 B2 | 4/2014 | Schlessinger et al. | |
| 8,846,063 B2 | 9/2014 | Seidling et al. | |
| 8,900,554 B2 | 12/2014 | Tamarkin et al. | |
| 9,320,705 B2 | 4/2016 | Tamarkin et al. | |
| 9,345,255 B2 | 5/2016 | Kindel et al. | |
| 9,364,402 B1 | 6/2016 | Garcia et al. | |
| 9,597,282 B2 | 3/2017 | Pagliuca et al. | |
| 9,603,817 B2 | 3/2017 | Bean et al. | |
| 9,642,792 B2 | 5/2017 | Tatsuguchi et al. | |
| 10,010,572 B2 | 7/2018 | Parris | |
| 10,117,812 B2 | 11/2018 | Tamarkin et al. | |

(Continued)

FOREIGN PATENT DOCUMENTS

| | | |
|---|---|---|
| CN | 105998199 A | 10/2016 |
| CN | 109481659 A | 3/2019 |

(Continued)

OTHER PUBLICATIONS

"Takasago Sensates", Lipo Chemicals, 2003.
"Trends and Formulation Strategies for Topical Drugs", Pharmaceutical Technology, BASF, May 2018, 1-36.
Anhydrous Gel: Fast absorption, Reduced Gloss, Vitamin C Stabilization, Dow Coming Corporation, 2016.
Cutaneous Sensory Systems, Elsevier, 2012, 321-331.
Andersson H., et al. (Jun. 9, 2004). "Activation by Menthol, Icilin, and Cold is Differentially Modulated by Intracellular pH", The Journal of Neuroscience, 24 / 23, 5364-5369.
Andrade E.L. et al. (2012). "TRPA1 Antagonists as Potential Analgesic Drugs", Pharmacology & Therapeutics, 133, 189-204.
Barkin; R. L (Jul. 2013). "The Pharmacology of Topical Analgesics", Postgraduate Medicine, 12(4): 7-18.

(Continued)

*Primary Examiner* — Jake M Vu

(57) ABSTRACT

Provided are topical analgesic gel compositions having relatively high payloads of menthol and camphor by microemulsion technology and methods of preparing topical analgesic gel compositions having relatively high payloads of menthol and camphor. Topical analgesic gel compositions may include from 12 to 16 wt. % menthol; from 4 to 8 wt. % camphor; from 0.1 to 2 wt. % carbomer; and 60 to 70 wt. % solvent. Topical analgesic gel compositions can have a viscosity from 60,000 to 110,000 centipoise.

15 Claims, 1 Drawing Sheet

(56) References Cited

U.S. PATENT DOCUMENTS

| 10,494,330 | B2 | 12/2019 | Itoh et al. | |
|---|---|---|---|---|
| 10,576,047 | B2 | 3/2020 | Maniar | |
| 11,617,727 | B2 * | 4/2023 | Das | A61K 36/55 |
| | | | | 514/692 |
| 12,097,186 | B2 * | 9/2024 | Das | A61K 47/44 |
| 2006/0057075 | A1 | 3/2006 | Arkin et al. | |
| 2006/0269500 | A1 | 11/2006 | Riemer et al. | |
| 2009/0264839 | A1 | 10/2009 | Kriksunov et al. | |
| 2014/0086857 | A1 | 3/2014 | Blizzard | |
| 2014/0348959 | A1 | 11/2014 | Mitchnick et al. | |
| 2015/0119369 | A1 | 4/2015 | Harrison et al. | |
| 2015/0141389 | A1 | 5/2015 | Aliyar et al. | |
| 2016/0106690 | A1 | 4/2016 | Bucks et al. | |
| 2016/0220475 | A1 | 8/2016 | Scherner et al. | |
| 2017/0071874 | A1 * | 3/2017 | Aranki | A61K 36/53 |
| 2017/0274084 | A1 | 9/2017 | Friedman et al. | |
| 2017/0340649 | A1 | 11/2017 | Rana et al. | |
| 2017/0348418 | A1 | 12/2017 | Tamarkin et al. | |
| 2018/0042832 | A1 | 2/2018 | Kalem et al. | |
| 2018/0185429 | A1 | 7/2018 | Iyer | |
| 2018/0311184 | A1 | 11/2018 | Hoag | |
| 2018/0311274 | A1 | 11/2018 | Majhi | |
| 2019/0022000 | A1 | 1/2019 | Tamarkin et al. | |
| 2019/0029958 | A1 | 1/2019 | Tamarkin et al. | |
| 2019/0046438 | A1 | 2/2019 | Hnat | |
| 2019/0060193 | A1 | 2/2019 | Schmaus et al. | |
| 2019/0076339 | A1 | 3/2019 | Tamarkin et al. | |
| 2019/0142710 | A1 | 5/2019 | Hedren et al. | |
| 2019/0209442 | A1 | 7/2019 | Syed et al. | |
| 2019/0343116 | A1 | 11/2019 | Fuoco | |

FOREIGN PATENT DOCUMENTS

| EP | 0698393 | A1 | 2/1996 |
|---|---|---|---|
| EP | 0988852 | A2 | 3/2000 |
| EP | 1066827 | A2 | 1/2001 |
| EP | 1019024 | B1 | 1/2004 |
| EP | 1393716 | A2 | 3/2004 |
| EP | 1947934 | A2 | 7/2008 |
| EP | 2457555 | A2 | 5/2012 |
| EP | 2061432 | B1 | 12/2012 |
| EP | 2101819 | B1 | 1/2013 |
| EP | 1583566 | B1 | 2/2013 |
| EP | 2620137 | A1 | 7/2013 |
| EP | 1556009 | B1 | 12/2014 |
| EP | 2841106 | A1 | 3/2015 |
| EP | 2928450 | A1 | 10/2015 |
| EP | 1699433 | B1 | 5/2017 |
| EP | 2928451 | B1 | 7/2017 |
| EP | 3211064 | A1 | 8/2017 |
| EP | 3219303 | A1 | 9/2017 |
| EP | 3355874 | A4 | 6/2019 |
| EP | 1556009 | B2 | 7/2021 |
| GB | 1042529 | A | 9/1966 |
| GB | 1465665 | A | 2/1977 |
| JP | S63119420 | A | 5/1988 |
| JP | H07103031 | B2 | 11/1995 |
| JP | 2000225360 | A | 8/2000 |
| KR | 100625741 | B1 | 9/2006 |
| WO | 2007056491 | A2 | 5/2007 |
| WO | 2011014850 | A2 | 2/2011 |
| WO | 2013036961 | A1 | 3/2013 |
| WO | 2015079233 | A1 | 6/2015 |
| WO | 2018085535 | A2 | 5/2018 |
| WO | 2019014380 | A1 | 1/2019 |
| WO | 2019170195 | A1 | 9/2019 |
| WO | 2019178360 | A1 | 9/2019 |

OTHER PUBLICATIONS

Biswal B., el. al. (Dec. 2014). "Formulation and Evaluation of Microemulsion Based Topical Hydrogel Containing Lornoxicam", Journal of Applied Pharmaceutical Science, 4(12): 77-84.
Choudhury H., et al. (Apr. 12, 2017). "Recent Update on Nanoemulgel as Topical Drug Delivery System", Journal of Pharmaceutical Sciences, Elsevier, 106: 1736-1751.
De Cassia Da Silveira E SA R.; et al. (Jan. 18, 2013). "A Review on Anti-Inflammatory Activity of Monoterpenes", Molecules, 18, 1227-1254.
Draelos Z.D.; Md., "Botanicals as Topical Agents", Clinics in Dermatology, Elsevier, Copyright 2001, 19, 474-477.
Frederiksen K; et al. (Jan. 14, 2015). "Formulation considerations in the design of topical, polymeric film-forming systems for sustained drug delivery to the skin", European Journal of Pharmaceutics and Biopharmaceutics, 91, 9-15.
Galeotti N., et al. (2002). "Menthol: a natural analgesic compound", Neuroscience Letters, Elsevier, 322, 145-148.
Hayman M, et al. (2008). Capsaicin: A review of its pharmacology and clinical applications, Current Anaesthesia & Critical Care, Elsevier, 19, 338-343.
International Search Report & Written Opinion mailed Jul. 21, 2020 from corresponding PCT Application PCT/US2020/029485 filed Apr. 23, 2020.
Kathe, K. et al. (2017). "Film Forming Systems for Topical and Transdermal Drug Delivery", Asian Journal of Pharmaceutical Sciences, 1-11.
Kumar, S. (2014). "The Importance of Antioxidant and Their Role in Pharmaceutial Science—A Review", Asian Journal of Research in Chemistry and Pharmaceutical Sciences, 1/1, 27-44.
Leffingwell, J.C. (2009). "Cooling ingredients and Their Mechanism of Action", Cosmetic Science and Technology, 661-675.
Mccurdy, C.R. et al. (2005). Analgesic Substances Derived from Natural Products (natureceuticals), Life Sciences, 476-484.
Park B, et al. (Sep. 2013). "Cooling the Skin: Understanding a Specific Cutaneous Thermosensation", Journal of LifestyleMedicine, 2(3): 91-97.
Shirai, T. et al. (May 31, 2017). "Identification of a Novel TRPM8 Agonist from Nutmeg: A Promising Cooling Compound", ACSMedicinal Chemistry Letters, 8: 715-719.
Siyeon, K. et al. (May 9, 2018). "L-Menthol Attenuates the Magnitude of Cold-induced Vasodilation on the Extremities of Young? emales", Journal of Physiological Anthropology, 37(14): 1-8.
Turek, C. et al. (2013). "Stability of Essential Oils: A Review", Comprehensive Reviews in Food Science and Food Safety, 12, 40-53.
Watson, P. (Oct. 7, 1994). "Topical Capsaicin as an Adjuvant Analgesic", Journal of Pain and Symptom Management, 9: 425-433.
Webster, G. et al. (2012). "Selection of Pharmaceutical Antioxidants by Hydrodynamic Voltammetry," Electroanalysis, 24 (6): 1394-1400.
Aerosol Supplies Australia Pty Ltd, "Safety Data Sheet Isopentane (20-85%/A31 (15-80%)", 2016, from: https://static1. squarespace. com/static/59dd7c7b49fc2bf4afd79a38/t/5d8abc737c1cc52e1383a193/1569373304566/ASA+Isopentane+%2820-85%25%29+A31+%2815-80%25%29+Australian+GHS+SDS+2016.pdf (Year: 2016).
Arthiritis Foundation., Anti-Inflammatory Benefits of Flaxseed, 2016.
ATPextreme, "What is Vasodilation and how is it beneficial to atheletes", 2014; screenshot of Wayback Machine from https://atpextreme.com/what-is-vasodilation-and-how-is-it-beneficial-to-athletes/). (Year: 2014).
Canada, "Summary Safety Review—Over-the-Counter Topical Pain Relievers Containing Menthol, Methyl Salicylate or Capsaicin—Assessing the Risk of Serious Skin Burns", 2017, Government of Canada (Year: 2017).
Dermatology Times, "What are sensates in moisturizers and what is their value?", 2017, Dermatology Times, from https://www.dermatologytimes.com/view/what-are-sensates-moisturizers-and-what-their-value (Year: 2017).
Drugbank., Glycol salicylate, 2021.
Holzer, "The pharmacological challenge to tame the transient receptor potential vanilloid-1 (TRP1) nocisensor", 2008, British Journal of Pharmacology, 155, 1145-1162 (Year: 2008).

(56)          References Cited

OTHER PUBLICATIONS

International Search Report and Written Opinion, mailed Jul. 23, 2020, for PCT Application No. PCT/US2020/029439, filed Apr. 23, 2020, 13 pages.

Lapczynski, "Fragrance material review on methyl salicylate", 2007, Food and Chemical Toxicology, 45, S428-S452 (Year: 2007).

Mary Ann Liebert, Inc. Publishers, "Final report of the safety assessment of isobutane, isopentane, n-butane, and propane", 1982, Journal of the American College of Toxicology, 1, 127-142 (Year: 1982).

Parchem, Vinyl Caprolactam/PVP/Dimethylaminoethyl Methacrylate Copolymer, 2022; from: https://www.parchem.com/chemical-supplier-distributor/Vinyl-caprolactam-PVP-dimethylaminoethyl-methacrylate-copolymer-095836.aspx (Year: 2022).

Saijo S., Machine translation of JP 2000225360A, Google Patents, 2000.

Specialchem: "Film Formers," 2014, 1 Page, (Screenshot From Wayback Machine), Retrieved from URL: https://cosmetics.specialchem.com/product-categories/ingredients-film-formers.

* cited by examiner

TOPICAL ANALGESIC GEL COMPOSITIONS

CROSS-REFERENCE TO RELATED APPLICATIONS

This application is a continuation application of U.S. patent application Ser. No. 16/856,176, filed Apr. 23, 2020, which claims the benefit of priority to U.S. Provisional Application No. 62/841,103, filed Apr. 30, 2019, the disclosures of which are herein incorporated by reference in their entirety.

FIELD OF THE INVENTION

This relates to topical analgesic compositions, and more particularly, to topical analgesic gel compositions having a high payload of active ingredient(s).

BACKGROUND OF THE INVENTION

Topical analgesics are often used to help treat musculoskeletal injuries and disorders, including pulled muscles, sprained muscles, and arthritis. Some formulations of topical analgesics provide warming or cooling sensation in the area of application. When applied to an area of discomfort on the skin, the active ingredient(s) in the topical analgesic composition react to produce a cool feeling, and then a warm feeling on the surface of the skin. Muscles proximate to the cooling/warming sensation send signals to area nerve receptors. These signals are sent from the nerve receptors to the nerve fibers until they reach the brain. Thus, when a patient applies a topical analgesic to an area of pain, the cooling/warming sensations of the topical analgesic distract the brain from any pain signals it may be receiving from that same area of the skin. This in turn distracts the patient from his or her aches or pains.

SUMMARY OF THE INVENTION

Provided are topical analgesic gel compositions and methods for preparing topical analgesic gel compositions. In particular, topical analgesic gel compositions provided herein can have a high payload of active ingredient(s) without the use of fats or waxes that are solid at room temperature. Instead, topical analgesic gel compositions provided herein use alcohol and glycols (e.g., pentylene glycol & glycerin) as solvents to solubilize a mixture of menthol and camphor. Additionally, without incorporating fats or waxes, topical analgesic gel compositions provided herein have the additional benefit of providing a non-greasy, non-oily feel on the skin.

Unlike topical analgesic gel compositions provided herein, conventional topical analgesic compositions generally include fats and/or waxes. These fats or waxes in conventional topical analgesic compositions are emulsified in water to provide a micro-emulsion with a cream-like structure. The fats and/or waxes also form an occlusive barrier to the skin. Additionally, only by using fats and/or waxes can conventional topical analgesic compositions achieve a high payload of menthol and/or camphor (i.e., the fats or waxes act as a carrier for the active ingredients(s)). However, due to the fats and/or waxes in conventional topical analgesic compositions, these formulations are generally not easy to spread into the skin and have a greasy or oily appearance when applied to the skin.

Topical analgesic gel compositions provided herein are formulated without the use of any fats or waxes such that they do not have a greasy or oily character when applied to the skin. The absence of fats or waxes also contributes to topical analgesic gel compositions that can be spread onto the skin relatively easily and provide fast absorption of the active ingredient(s), essential oils, and sensates into the skin. Additionally, topical analgesic gel compositions provided herein can achieve a relatively high payload of active ingredients without using fats or waxes to carry the active ingredients. Instead, the compositions provided herein use alcohol and glycols (e.g., pentylene glycol & glycerin) as solvents to solubilize relatively high concentrations of menthol and camphor.

Accordingly, provided herein are topical analgesic gel compositions that do not impart a greasy or oily feel on the skin, yet can achieve a relatively high payload of active ingredient(s) without comprising fats or waxes.

In some embodiments, a topical analgesic gel composition is provided, the topical analgesic gel composition comprising: 12 to 16 wt. % menthol; 4 to 8 wt. % camphor; 0.1 to 2 wt. % carbomer; and 60 to 70 wt. % solvent, wherein the topical analgesic composition has a viscosity from 60,000 to 110,000 centipoise.

In some embodiments of the topical analgesic gel composition, the topical analgesic gel composition does not comprise a fat or a wax that is solid at room temperature.

In some embodiments of the topical analgesic gel composition, a total amount of the amount of menthol and the amount of camphor comprises 21 wt. % or more.

In some embodiments of the topical analgesic gel composition, the topical analgesic gel composition has a pH of 5 to 5.5.

In some embodiments of the topical analgesic gel composition, the topical analgesic gel composition has a specific gravity from 0.9 to 1.0.

In some embodiments of the topical analgesic gel composition, the topical analgesic gel composition is formed by a process comprising forming a eutectic mixture comprising menthol and camphor.

In some embodiments of the topical analgesic gel composition, the topical analgesic gel composition comprises from 0.5 to 1.5 wt. % sensate.

In some embodiments of the topical analgesic gel composition, the sensate comprises one or more of menthoxypropanediol, isopulegol, or vanillyl butyl ether.

In some embodiments of the topical analgesic gel composition, the topical analgesic gel composition comprises 0.1 to 1% of one or more essential oils.

In some embodiments of the topical analgesic gel composition, the one or more essential oils comprises one or more of peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil, and frankincense (*Olibanum* or *Boswellia carterii*) oil.

In some embodiments of the topical analgesic gel composition, the solvent comprises an alcohol.

In some embodiments of the topical analgesic gel composition, the solvent comprises water.

In some embodiments of the topical analgesic gel composition, the topical analgesic gel composition comprises 0.1 to 1 wt. % neutralizing agent.

In some embodiments of the topical analgesic gel composition, the topical analgesic gel composition comprises 1 to 3 wt. % one or more surfactants.

In some embodiments of the topical analgesic gel composition, the topical analgesic gel composition comprises 1 to 5 wt. % glycerin.

In some embodiments of the topical analgesic gel composition, the topical analgesic gel composition comprises 1 to 3 wt. % penetration enhancer.

In some embodiments of the topical analgesic gel composition, the topical analgesic gel composition comprises droplets having an average droplet size of 1 to 5 microns.

In some embodiments, a method for treating muscle and joint ache or pain is provided, the method comprising administering to a patient in need thereof a topical analgesic gel composition according to any one of the topical analgesic composition embodiments.

In some embodiments, a topical analgesic gel product is provided, the topical analgesic gel product comprising: a tube applicator; and a topical analgesic gel composition comprising: 12 to 16 wt. % menthol; 4 to 8 wt. % camphor; 0.1 to 2 wt. % carbomer; and 60 to 70 wt. % solvent, wherein the topical analgesic gel composition has a viscosity from 60,000 to 110,000 centipoise and the topical analgesic gel composition is contained within the tube applicator to form a topical analgesic product.

In some embodiments of the topical analgesic gel product, the topical analgesic gel composition does not comprise a fat or a wax that is solid at room temperature.

In some embodiments of the topical analgesic gel product, a total amount of the amount of menthol and the amount of camphor comprises 21 wt. % or more of the topical analgesic gel composition.

In some embodiments of the topical analgesic gel product, the topical analgesic gel composition has a pH of 5 to 5.5.

In some embodiments of the topical analgesic gel product, the topical analgesic gel composition has a specific gravity of 0.9 to 1.0.

In some embodiments of the topical analgesic gel product, the topical analgesic gel composition is formed by a process comprising forming a eutectic mixture comprising menthol and camphor.

In some embodiments of the topical analgesic gel product, the topical analgesic gel product comprises 0.5 to 1.5 wt. % sensate.

In some embodiments of the topical analgesic gel product, the sensate comprises one or more of menthoxypropanediol, isopulegol, or vanillyl butyl ether.

In some embodiments of the topical analgesic gel product, the topical analgesic gel product comprises 0.1 to 1% of one or more essential oils.

In some embodiments of the topical analgesic gel product, the one or more essential oils comprises one or more of peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil, and frankincense (*Olibanum* or *Boswellia carterii*) oil.

In some embodiments of the topical analgesic gel product, the solvent comprises an alcohol.

In some embodiments of the topical analgesic gel product, the solvent comprises water.

In some embodiments of the topical analgesic gel product, the topical analgesic gel composition comprises 0.1 to 1 wt. % neutralizing agent.

In some embodiments of the topical analgesic gel product, the topical analgesic gel composition comprises 1 to 3 wt. % one or more surfactants.

In some embodiments of the topical analgesic gel product, the topical analgesic gel composition comprises 1 to 5 wt. % glycerin.

In some embodiments of the topical analgesic gel product, the topical analgesic gel composition comprises 1 to 3 wt. % penetration enhancer.

In some embodiments of the topical analgesic gel product, the topical analgesic gel composition comprises droplets having an average droplet size of 1 to 5 microns.

In some embodiments, a method for treating muscle and joint ache or pain is provided, the method comprising administering to a patient in need thereof a topical analgesic gel product according to any one of the topical analgesic gel product embodiments.

In some embodiments, a method of preparing a topical analgesic gel composition is provided, the method comprising: preparing a mixture comprising menthol and camphor; and adding a solvent and a carbomer to the mixture comprising menthol and camphor to form a topical analgesic gel composition.

In some embodiments of the method of preparing a topical analgesic gel composition, the topical analgesic gel composition does not comprise a fat or a wax that is solid at room temperature.

In some embodiments of the method of preparing a topical analgesic gel composition, preparing a mixture comprising menthol and camphor comprises preparing a eutectic mixture comprising menthol and camphor.

In some embodiments of the method of preparing a topical analgesic gel composition, the method comprises adding a sensate to the mixture comprising menthol and camphor.

In some embodiments of the method of preparing a topical analgesic gel composition, adding a sensate to the mixture comprising menthol and camphor comprises adding one or more of menthoxypropanediol, isopulegol, and vanillyl butyl ether to the mixture comprising menthol and camphor.

In some embodiments of the method of preparing a topical analgesic gel composition, the method comprises adding one or more essential oils to the mixture comprising menthol and camphor.

In some embodiments of the method of preparing a topical analgesic gel composition, adding one or more essential oils to the mixture comprising menthol and camphor comprises adding one or more of peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil, and frankincense (*Olibanum* or *Boswellia carterii*) oil to the mixture comprising menthol and camphor.

In some embodiments of the method of preparing a topical analgesic gel composition, the topical analgesic gel composition comprises 12 to 16 wt. % menthol.

In some embodiments of the method of preparing a topical analgesic gel composition, the topical analgesic gel composition comprises 4 to 8 wt. % camphor.

In some embodiments of the method of preparing a topical analgesic gel composition, the topical analgesic gel composition comprises 0.1 to 2 wt. % carbomer.

In some embodiments of the method of preparing a topical analgesic gel composition, the topical analgesic gel composition comprises 60 to 70 wt. % solvent.

In some embodiments of the method of preparing a topical analgesic gel composition, the solvent comprises an alcohol.

In some embodiments of the method of preparing a topical analgesic gel composition, the topical analgesic gel composition has a viscosity from 60,000 to 110,000 centipoise.

In some embodiments of the method of preparing a topical analgesic gel composition, the topical analgesic gel composition has a specific gravity of 0.9 to 1.

In some embodiments of the method of preparing a topical analgesic gel composition, the topical analgesic gel composition has a pH of 5 to 5.5.

In some embodiments of the method of preparing a topical analgesic gel composition, the topical analgesic gel composition comprises 0.5 to 1.5 wt. % sensate.

In some embodiments of the method of preparing a topical analgesic gel composition, the sensate comprises one or more of menthoxypropanediol, isopulegol, or vanillyl butyl ether.

In some embodiments of the method of preparing a topical analgesic gel composition, the topical analgesic gel composition comprises 0.1 to 1 wt. % neutralizing agent.

In some embodiments of the method of preparing a topical analgesic gel composition, the topical analgesic gel composition comprises 1 to 3 wt. % one or more surfactants.

In some embodiments of the method of preparing a topical analgesic gel composition, the topical analgesic gel composition comprises 1 to 5 wt. % glycerin.

In some embodiments of the method of preparing a topical analgesic gel composition, the topical analgesic gel composition comprises 1 to 3 wt. % penetration enhancer.

In some embodiments of the method of preparing a topical analgesic gel composition, the topical analgesic gel composition comprises droplets having an average droplet size of 1 to 5 microns.

BRIEF DESCRIPTION OF THE DRAWINGS

Various embodiments are described with reference to the accompanying figures, in which.

DETAILED DESCRIPTION OF THE INVENTION

Figure 1:
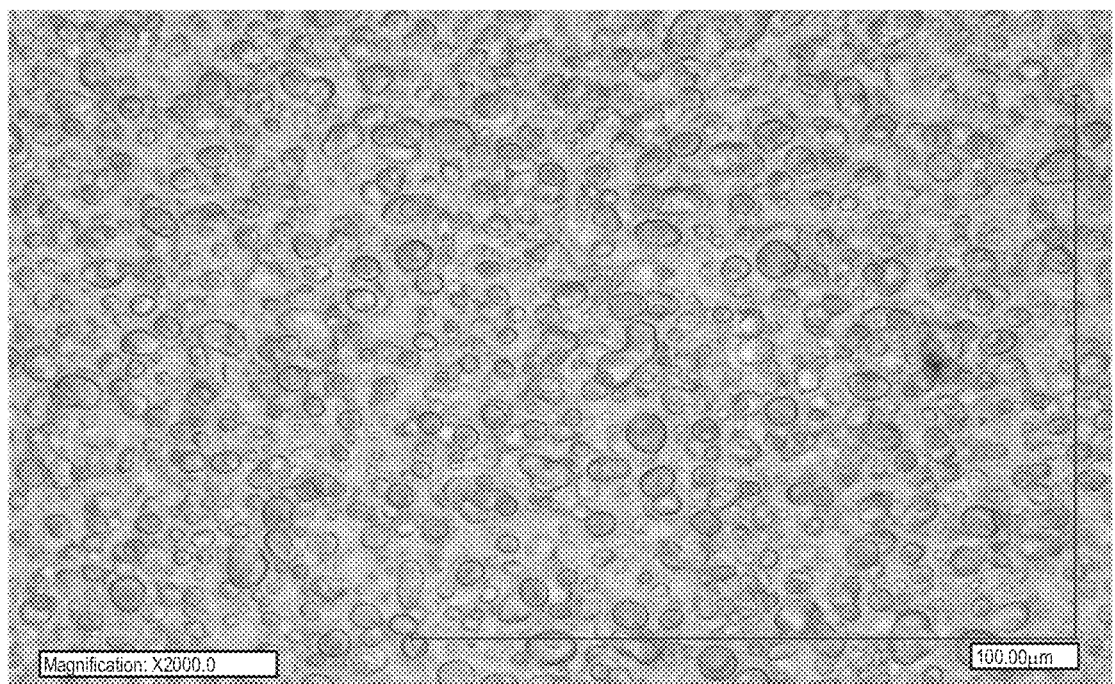
FIG. 1 provides a magnified image of a topical analgesic gel composition, according to some embodiments.

Described herein are topical analgesic gel compositions and methods of making topical analgesic gel compositions. As described above, conventional topical analgesic compositions comprise fats or waxes that provide a greasy, oily feel on application and can only achieve high payloads of menthol and/or camphor with solid fats or waxes to act as a carrier for the active ingredient(s). However, topical analgesic gel compositions according to embodiments provided herein are formulated without solid fats or waxes such that they do not impart a greasy or oily feel on application. Additionally, topical analgesic gel compositions provided herein can include a relatively high payload of menthol and/or camphor without using solid fats or waxes as a carrier.

Notably, relatively high loading of menthol and camphor has been achieved without the use of solid fats or waxes as a carrier for the menthol and/or camphor. Specifically, topical analgesic gel compositions disclosed herein can achieve a high payload of menthol and/or camphor by using an alcohol (e.g. ethanol) as a solvent to solubilize the menthol and/or camphor. Unlike topical analgesic gel compositions disclosed herein, conventional topical analgesic compositions typically use water as the primary solvent. However, menthol and camphor are not soluble in water, especially in the high concentrations needed for formulations having a high payload of menthol and/or camphor.

Further, topical analgesic gel compositions provided herein may be used in conjunction with a tube applicator or a roll-on applicator. Because topical analgesic gel compositions disclosed have a light and easily spreadable character and do not comprise solid fats or waxes, the compositions may be compatible with a tube or a roll-on applicator. Conversely, formulations comprising solid fats or waxes cannot be used with a roll-on applicator because they tend to "crack" or agglomerate due to the shear force applied during application by the roller ball of the roll-on applicator. Additionally, formulations comprising solid fats or waxes do not spread easily when applied from a roll-on applicator and require a user to rub the formulation into his or her skin with a hand. Topical analgesic gel composition described here can also be packaged and administered in various different ways, including in a tube or in a roll-on applicator.

Additionally, topical analgesic gel compositions provided herein may be classified as a stable micro-emulsion. As described in more detail below, the active ingredients (e.g., menthol, camphor), the sensates, and the essential oils of a topical analgesic gel composition form small, microscopic droplets. These micron-sized droplets are emulsified/stabilized in the hydro-alcoholic cream base, and may not coalesce or break. This micro-emulsion comprising the small droplets of actives, essential oils, and sensates can lead to faster absorption to skin than a composition having larger droplets. Small droplet sizes can also enhance the stability of the topical analgesic gel composition, leading to an increased shelf life. Additionally, the small droplet size lends itself to a less greasy formulation that disappears faster without being rubbed off on clothing or other parts of the body during application. Thus, the small droplet size contributes to several beneficial characteristics of the topical analgesic gel compositions provided herein. In some embodiments, the average droplet size may be from 0.1 to 50 microns, from 0.5 to 25 microns, or from 1 to 5 microns. In some embodiments, the average droplet size may be less than 50 microns, less than 40 microns, less than 30 microns, less than 20 microns, less than 10 microns, less than 5 microns, less than 3 microns, less than 1 micron, or less than 0.5 microns. In some embodiments the average droplet size may be more than 0.1 microns, more than 0.5 microns, more than 1 micron, more than 3 microns, more than 5 microns, more than 10 microns, more than 20 microns, more than 30 microns, or more than 40 microns.

Provided below is a discussion of topical analgesic gel compositions, topical analgesic gel compositions as provided in a tube applicator, and methods for preparing topical analgesic gel compositions.

Topical Analgesic Gel Compositions

Provided below is a discussion of topical analgesic gel compositions according to some embodiments. In some embodiments, a topical analgesic gel composition can include an active ingredient (e.g., menthol, camphor), a sensate, an essential oil blend, a polymeric viscosity builder, a chelating agent, a fragrance blend, a neutralizing agent, a penetration enhancer, and/or a solvent.

In some embodiments, topical analgesic gel compositions can comprise an organoleptic composition. An organoleptic composition may comprise cooling and warming sensates, an essential oil mixture comprising one or more essential oils, vitamin E, linseed oil, and optionally also further excipients. Organoleptic compositions provided herein can add to the sensation of long-lasting pain-relieving effect, to provide a pleasant fragrance as a mask, and/or to complement the natural scent of menthol and/or camphor. Organoleptic compositions are described in detail further below.

Specifically, the materials of topical analgesic gel compositions presented below are discussed by way of the following categories: (1) active ingredients; (2) organoleptic compositions; and (3) additional ingredients. Further, ingredients introduced and discussed with respect to organoleptic compositions are described briefly with respect to topical analgesic gel compositions comprising an organoleptic composition (i.e., these materials are described with respect to the topical analgesic gel composition as a whole). Each category is described in turn below.

Active Ingredients

Numerous different active ingredients may be used in the topical analgesic gel compositions provided herein. Menthol and/or camphor may be used, as discussed above. In addition, histamine dihydrochloride, capsaicin, methyl salicylate, methyl nicotinate may also be used in some embodiments. Topical analgesic gel compositions provided herein may include menthol, camphor, histamine dihydrochloride, capsaicin, methyl salicylate, and/or methyl nicotinate.

In some embodiments, a topical analgesic gel composition may include menthol. Menthol can be naturally obtained from the oils of corn mint, peppermint, and other mints, or menthol can be obtained as a synthetic product. Menthol is commonly used in topical analgesics because it has local anesthetic (i.e., a medication that causes the absence of pain sensations) and counterirritant (i.e., a substance that creates irritation or mild inflammation in one location to lessen discomfort or inflammation in a second location) properties. If the concentration of menthol in a topical analgesic gel composition is too high, it can cause irritation or chemical burning. If the concentration is too low, the topical analgesic gel composition may be less effective than desired, or even ineffective at providing a cooling sensation to a user. In some embodiments, a topical analgesic gel composition may comprise from 3 to 30 wt. %, from 5 to 25 wt. %, from 10 to 20 wt. %, or from 14 to 18 wt. % menthol. In some embodiments, a topical analgesic gel composition may comprise less than 30 wt. %, less than 25 wt. %, less than 20 wt. %, less than 18 wt. %, less than 15 wt. %, less than 12 wt. %, less than 10 wt. %, or less than 5 wt. % menthol. In some embodiments, a topical analgesic gel composition may comprise more than 3 wt. %, more than 5 wt. %, more than 10 wt. %, more than 12 wt. %, more than 15 wt. %, more than 18 wt. %, more than 20 wt. %, or more than 25 wt. % menthol.

In some embodiments, a topical analgesic gel composition may include camphor. Camphor is a terpinoid found in the wood of camphor laurel, an evergreen tree, kapur tree, or a timber tree. Camphor can also be obtained synthetically. Camphor is readily absorbed in the skin and produces a warming sensation when vigorously applied, or a cooling sensation when gently applied. It can also produce a local analgesia effect. Like menthol, it also has counterirritant properties. Topical analgesic gel compositions comprising high concentrations of camphor may cause skin redness, skin irritations, or chemical burns. Topical analgesic gel compositions comprising too little camphor may be less effective than desired, or even ineffective at providing a warming sensation to a user. In some embodiments, a topical analgesic gel composition may comprise from 1 to 20 wt. %, from 3 to 15 wt. %, from 5 to 10 wt. %, or from 5 to 6 wt. % camphor. In some embodiments, a topical analgesic gel composition may comprise less than 20 wt. %, less than 18 wt. %, less than 15 wt. %, less than 12 wt. %, less than 10 wt. %, less than 8 wt. %, less than 6 wt. %, or less than 5 wt.

% camphor. In some embodiments, a topical analgesic gel composition may comprise more than 3 wt. %, more than 5 wt. %, more than 6 wt. % more than 8 wt. %, more than 10 wt. %, more than 12 wt. %, more than 15 wt. %, or more than 18 wt. % camphor.

In some embodiments, the combination of menthol and camphor can form a eutectic mixture. A eutectic mixture is a mixture having two or more components that has a lower melting point than the separate melting points of its individual constituents. Although menthol and camphor are individually solid at room temperature, the combination of menthol and camphor is known to form liquid, eutectic mixtures at certain ratios. In some embodiments, certain combinations of concentrations of menthol and camphor may be particularly suitable for the topical analgesic gel compositions as described herein, including, but not limited to, concentrations that result in a eutectic mixture of menthol and camphor. These eutectic mixtures may be more readily formulated than the corresponding non-eutectic compositions, as the liquid phase of the eutectic mixture promotes uniform distribution of the active ingredients throughout the formulation and facilitates absorption into the skin upon application for a rapid pain relieving effect.

In some embodiments, a topical analgesic gel composition may include from 5 to 35 wt. %, from 15 to 35 wt. %, or from 20 to 25 wt. % menthol-camphor mixture. In some embodiments, a topical analgesic gel composition may include more than 5 wt. %, more than 10 wt. %, more than 15 wt. %, more than 20 wt. %, more than 25 wt. %, or more than 30 wt. % menthol-camphor mixture. In some embodiments, a topical analgesic gel composition may include less than 35 wt. %, less than 30 wt. %, less than 25 wt. %, less than 20 wt. %, less than 15 wt. %, or less than 10 wt. % menthol-camphor mixture. If the menthol-camphor mixture is much greater than 35 wt. %, the mixture may have difficulties mixing into solution with the solvent and other components of topical analgesic gel compositions provided herein.

Organoleptic Compositions

As described above, some embodiments of topical analgesic gel compositions may include an organoleptic composition. Organoleptic compositions provided herein may be incorporated into topical analgesic gel compositions to add to the sensation of long-lasting pain-relieving effect, to provide a pleasant fragrance as a mask, and/or to complement the natural scent of menthol and camphor. In some embodiments, organoleptic compositions can include cooling and warming sensates, an essential oil mixture, linseed oil, and optionally also further excipients (e.g., vitamin E oil, surfactants, penetration enhancers).

In some embodiments, an organoleptic composition comprises one or more sensates. Sensates, or sensory agents, are compounds that provide a cool or warming effect when applied to the skin. In particular, sensates function by directly stimulating the receptors at the nerve endings of the skin to produce a cooling or warming sensation. One or more sensates may be selected from the group consisting of cooling sensates, warming sensates, and any combinations or mixtures thereof. Suitable cooling and warming sensates may include, but are not limited to, menthol and menthol derivatives (e.g., isomenthol, neomenthol, neoisomenthol, menthoglycol para-menthoxy-3,8-propanediol, isopulegol, menthoxypropanediol), capsaicin, other capsaicinoids (e.g., dihydrocapsaicin, nordihydrocapsaicin, homocapsaicin, and homodihydrocapsaicin), eucalyptol, cinnamaldehyde, vanilloid derivatives such as vanillyl alcohol alkyl ethers (e.g., vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol n-hexyl ether, vanillyl amyl ether, vanillyl alcohol methyl ether, vanillyl alcohol ethyl ether, vanillyl isoamyl ether, vanillyl butyl ether), gingerol, zingerone, shogaol, piperine, icilin, and any combinations thereof. In some embodiments, the organoleptic composition comprises menthoxypropanediol (Coolact® 10), isopulegol (Coolact® P), icilin, or a combination thereof, as cooling sensates. In some embodiments, the organoleptic composition comprises vanillyl butyl ether (Hotact® VBE), cinnamaldehyde, or piperine, or a combination thereof, as warming sensates.

For example, menthoxypropanediol is a sensate and synthetic derivative of menthol that can provide a cooling sensation when applied to the skin. The compound acts as a cooling agent by stimulating the receptors at the nerve endings of the skin where applied to produce a cooling sensation. Menthoxypropanediol can also be used as a fragrance or a masking ingredient in some formulations. Too much menthoxypropanediol can cause irritation and even chemical burning. Too little menthoxypropanediol in a topical analgesic formulation may render the formulation less effective at producing a cooling sensation. In some embodiments, a topical analgesic composition comprising the organoleptic composition provide herein includes from 2 to 40 wt. %, from 5 to 30 wt. %, or from 8 to 15 wt. % menthoxypropanediol. In some embodiments, an organoleptic composition comprises less than 40 wt. %, less than 35 wt. %, less than 30 wt. %, less than 25 wt. %, less than 20 wt. %, less than 15 wt. %, less than 10 wt. %, less than 8 wt. %, or less than 5 wt. % menthoxypropanediol. In some embodiments, an organoleptic composition comprises more than 2 wt. %, more than 5 wt. %, more than 8 wt. %, more than 10 wt. %, more than 15 wt. %, more than 20 wt. %, more than 25 wt. %, more than 30 wt. %, or more than 35 wt. % menthoxypropanediol.

Another example of a sensate is isopulegol. Isopulegol is a sensate that is a chemical precursor to menthol. It is a terpene found in cannabis and known for having a minty odor. However, isopulegol also has anxiolytic, gastroprotective, and anticonvulsive properties. When used in the topical analgesic compositions provided herein, isopulegol can be used as a sensate that provides a cooling effect to the skin. It can function as a sensate by directly stimulating the receptors at the nerve endings of the skin to produce a cooling sensation. Specifically, isopulegol can provide a similar cooling effect as menthol, but without the odor of menthol. Topical analgesic gel compositions having too much isopulegol can be irritating to the skin. However, topical analgesic gel compositions having too little isopulegol may render the formulation less effective at providing the desired cooling effect. In some embodiments, an organoleptic composition provided herein includes from 2 to 30 wt. %, from 3 to 20 wt. %, or from 5 to 10 wt. % isopulegol. In some embodiments, an organoleptic composition comprises less than 30 wt. %, less than 25 wt. %, less than 20 wt. %, less than 15 wt. %, less than 10 wt. %, less than 5 wt. %, or less than 3 wt. % isopulegol. In some embodiments, an organoleptic composition comprises more than 2 wt. %, more than 3 wt. %, more than 5 wt. %, more than 10 wt. %, more than 15 wt. %, more than 20 wt. %, or more than 25 wt. % isopulegol.

Vanillyl butyl ether is a sensate that provides a warming effect when applied to the skin. The warming effect of vanillyl butyl ether can occur immediately upon application, building rapidly within the first five minutes and lasting up to two hours. Compared to active ingredients that can produce a warming effect (e.g., capsaicin or capsicum extract), vanillyl butyl ether can be less irritating. That said, topical analgesic gel compositions comprising too much vanillyl butyl ether can still cause skin irritation and/or burning. Topical analgesic gel compositions comprising too little vanillyl butyl ether may render the formulation less effective at providing the desired warming effect. In some embodiments, an organoleptic composition provided herein includes from 0.01 to 10 wt. %, from 0.05 to 5 wt. %, or from 0.1 to 2 wt. % vanillyl butyl ether. In some embodiments, an organoleptic composition provide herein includes less than 10 wt. %, less than 8 wt. %, less than 5 wt. %, less than 3 wt. %, less than 2 wt. %, less than 1 wt. %, less than 0.5 wt. %, less than 0.1 wt. %, or less than 0.05 wt. % vanillyl butyl ether. In some embodiments, an organoleptic composition provide herein includes more than 0.01 wt. %, more than 0.05 wt. %, more than 0.1 wt. %, more than 0.5 wt. % more than 1 wt. %, more than 3 wt. %, less than 5 wt. %, or more than 8 wt. % vanillyl butyl ether.

In addition to individual chemical compounds that may provide a cooling or warming sensation, an organoleptic composition may also comprise naturally-derived extracts, roots, or resins containing one or more sensates. For example, in some embodiments, the organoleptic composition may comprise chili pepper (*Capsicum frutescens*) resin, ginger root extract and cinnamon cassia bark extract, or any combination thereof. Combinations of particular naturally-derived extracts, roots, or resins may also be known and referred to by known trade name(s). For example, Phytol™ Heat is suitable naturally-derived extract, root, and/or resin containing one or more sensates and includes a combination of chili pepper (*Capsicum frutescens*) resin, ginger root extract and cinnamon cassia bark extract.

In some embodiments, a complementary cooling effect to supplement the effects of camphor and menthol may be desired. Such complementary cooling effect may be achieved with particular combinations of certain cooling sensates that may be incorporated into the organoleptic composition, and ultimately the topical analgesic gel compositions. In some embodiments, the one or more sensates may include one or more of menthoxypropanediol, isopulegol, and icilin, or any combinations thereof.

In some embodiments, a complementary warming sensation is desired to supplement the effects of camphor and menthol. Similar combinations of warming sensates may be incorporated into an organoleptic composition and a topical analgesic gel composition to achieve the desired warming sensation. In some embodiments, the one or more sensates may include one or more of cinnamaldehyde, piperine, vanillyl butyl ether, or any combinations thereof.

A combined cooling and warming sensation may be desired in some topical analgesic compositions. To achieve a combined cooling and warming sensation, combinations of certain cooling and warming sensates may be incorporated into an organoleptic composition to achieve the mixed cooling/warming effect. In some embodiments, the organoleptic composition comprises one or more sensates including one or more of menthoxypropanediol, isopulegol, vanillyl butyl ether, a combination of chili pepper (*Capsicum frutescens*) resin, ginger root extract, Cinnamon cassia bark extract, or any combinations thereof. In certain embodiments, the one or more sensates can include menthoxypropanediol, isopulegol, and/or vanillyl butyl ether.

Essential oils may also be included in the organoleptic compositions as described herein to complement the effect of the menthol, camphor, and aforementioned sensates on hot and cold receptors in the skin and to imbue an overall pleasant fragrance to the topical analgesic compositions. In addition to their sensory attributes, the essential oils utilized in organoleptic compositions and/or topical analgesic gel compositions described herein may further provide anti-inflammatory, anti-oxidant and/or antinociceptive effects on the skin. In some embodiments, an organoleptic composition comprises one or more essential oils. For example, suitable essential oils may include peppermint (*Mentha piperita*) oil, eucalyptus (*Eucalyptus globulus*) oil, rosemary (*Rosmarinus officinalis*) oil, Tunisian rosemary (*Rosmarinus officinalis*) oil, Idaho rosemary (*Rosmarinus officinalis*) oil, clove (*Eugenia caryophyllata*) oil, Spanish marjoram (*Thymus mastichina*) oil, sweet marjoram (*Organum majorana*) oil frankincense (*Olibanum* or *Boswellia carterii*) oil, clove (*Syzygium aromaticum*) oil, Ceylon cinnamon (*Cinnamomum verum* or *zeylanicum*) oil, cardamom (*Elettaria cardamomum*) oil, Guatemalan cardamom (*Elettaria cardamomum*) oil, black pepper (*Piper nigrum*) oil, bay leaf (or bay laurel or *Laurus nobilis*) oil, cassia (*Cinnamomum cassia*) oil, ginger (*Zingiber officinale*) oil, Chinese ginger (*Zingiber officinale*) oil, lemongrass Cochin (*Cymbopogon citratus*) oil, fennel (*Foeniculum vulgare*) oil, basil (*Ocimum basilicum*) oil, spearmint (*Mentha spicata* or *cardiaca*) oil, Roman chamomile (*Anthemis nobilis* of *Chamaemelum nobile*) oil, sage (*Salvia officinalis* L.) oil, Spanish sage (*Salvia lavandulaefolia*) oil, clary sage (*Salvia sclarea*) oil, Bulgarian lavender (*Lavandula angustifolia* or *officinalis*) oil, and nutmeg (*Myristica fragrans*) oil.

As described above, combinations of sensates may be prepared to afford a cooling, warming or mixed cooling and warming sensation to the organoleptic composition, and ultimately also to topical analgesic gel compositions. Similarly, combinations of essential oils in an essential oil mixture may be prepared to supplement the cooling, warming, or mixed cooling and warming effects of the sensates. Certain combinations or blends of essential oils may be suitable for providing a cooling sensation and/or a warming sensation as desired. For example, in some embodiments wherein a warming sensation is desired, the essential oil mixture may comprise clove (*Eugenia caryophyllata*) oil, Ceylon cinnamon (*Cinnamomum verum* or *zeylanicum*) oil, cardamom (*Elettaria cardamomum*) oil, black pepper (*Piper nigrum*) oil, bay leaf (or bay laurel or *Laurus nobilis*) oil, cassia (*Cinnamomum cassia*) oil, and/or ginger (*Zingiber officinale*) oil. In other embodiments wherein a cooling sensation is desired, the essential oil mixture may comprise fennel (*Foeniculum vulgare*) oil, peppermint (*Mentha piperita*) oil, basil (*Ocimum basilicum*) oil, spearmint (*Mentha spicata* or *cardiaca*) oil, eucalyptus (*Eucalyptus globulus*) oil, sage (*Salvia officinalis* L.) oil, and/or nutmeg (*Myristica fragrans*) oil. When a mixed cooling and warming sensation is desired, an organoleptic composition may include an essential oil mixture comprising peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil, and/or frankincense (*Olibanum* or *Boswellia carterii*) oil. It should be recognized the essential oil mixtures tailored for cooling sensation, warming sensation, and mixed cooling and warming sensation can be combined with the respective combinations of sensates for cooling, warming, and mixed cooling and warming.

In some embodiments, an essential oil mixture comprising peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil, and/or frankincense (*Olibanum* or

*Boswellia carterii*) oil may provide a combined cooling and warming sensation. This combination of essential oils can also effectively mask the smell of menthol and/or camphor and is compatible with a variety of topical analgesic gel formulations.

In some embodiments, an organoleptic composition comprises from 1 to 30 wt. %, from 3 to 20 wt. %, or from 5 to 10 wt. % essential oil mixture. In some embodiments, an organoleptic composition comprises less than 30 wt. %, less than 25 wt. %, less than 20 wt. %, less than 15 wt. %, less than 10 wt. %, less than 5 wt. %, or less than 3 wt. % essential oil mixture. In some embodiments, an organoleptic composition comprises more than 1 wt. %, more than 2 wt. %, more than 3 wt. %, more than 5 wt. %, more than 10 wt. %, more than 15 wt. %, more than 20 wt. %, or more than 25 wt. % essential oil mixture.

It should be recognized that in certain embodiments wherein peppermint oil is included in the essential oil mixture, the peppermint oil may contribute to the total quantity of menthol in the overall topical analgesic formulation. As a result of the contribution of menthol from the peppermint oil, which may depend upon the source of the peppermint oil, the fraction of menthol in the peppermint oil and total concentration of the peppermint oil in the topical analgesic, the quantity of menthol added as an independent ingredient may be adjusted accordingly to achieve the desired concentration.

In some embodiments, an organoleptic composition comprises vitamin E. Vitamin E is a known antioxidant and may be included in the essential oil mixture to prevent oxidation of the individual essential oils for longer shelf life. Vitamin E may be included in an organoleptic composition as an antioxidant and emollient, independently of and in addition to any vitamin E already included in the essential oil mixture. Vitamin E broadly refers to a group of fat soluble compounds known as tocopherols and tocotrienols, which have free-radical scavenging properties, but as referred to herein may include any individual isomers (alpha, beta, gamma, delta) of tocopherol and/or tocotrienol, or any combinations thereof. In some embodiments, an organoleptic composition comprises from 1 to 20 wt. %, from 3 to 15 wt. %, or from 5 to 10 wt. % vitamin E. In some embodiments, an organoleptic composition comprises less than 20 wt. %, less than 15 wt. %, less than 10 wt. %, less than 8 wt. %, less than 5 wt. %, or less than 3 wt. % vitamin E. In some embodiments, an organoleptic composition comprises more than 1 wt. %, more than 3 wt. %, more than 5 wt. %, more than 8 wt. %, more than 10 wt. %, or more than 15 wt. % vitamin E.

Certain relative percentages of the individual essential oils (and vitamin E) may be especially complementary in fragrance and scent. Table 1 below provides one example of a complementary combination of the mixture of essential oils and vitamin E for use with mentholated and camphorated topical analgesic gel compositions. It should be recognized that the individual percentages of each of the essential oils may be varied to provide the desired complementary scent and sensation with respect to the other cooling and/or warming sensates, menthol, and camphor. For example, in some embodiments, the percentages of the essential oils shown in the table below may be varied within ±25%. In addition, it should be further recognized that the exemplary essential oil blend shown in the table below is not intended to be limiting and that the essential oils in the organoleptic composition may be substituted to provide greater cooling or warming effect as desired.

13

TABLE 1

| Example essential oil blend. | |
|---|---|
| International Nomenclature of Cosmetic Ingredient | % (with vitamin E) |
| Rosemary (Rosmarinus officinalis) leaf oil | 24.5 |
| Spanish marjoram (Thymus mastichina) flower oil | 24.5 |
| Peppermint (Mentha piperita) oil | 14.5 |
| Eucalyptus (Eucalyptus globulus) leaf oil | 14.5 |
| Clove (Eugenia caryophyllus) oil | 10.0 |
| Frankincense (Boswellia carterii) oil | 10.0 |
| Tocopherol | 2.0 |
| TOTAL | 100.0 |

In some embodiments, an organoleptic composition comprises linseed oil as an emollient. Linseed oil, also known as flaxseed oil or flax oil, contains a variety of triglycerides, including alpha-linoleic acid, which can help to moisturize skin and enhance skin feel of topical formulations. In some embodiments, an organoleptic composition provided herein includes from 0.01 to 10 wt. %, from 0.05 to 5 wt. %, or from 0.1 to 2 wt. % linseed oil. In some embodiments, an organoleptic composition provide herein includes less than 10 wt. %, less than 8 wt. %, less than 5 wt. %, less than 3 wt. %, less than 2 wt. %, less than 1 wt. %, less than 0.5 wt. %, less than 0.1 wt. %, or less than 0.05 wt. % linseed oil. In some embodiments, an organoleptic composition provide herein includes more than 0.01 wt. %, more than 0.05 wt. %, more than 0.1 wt. %, more than 0.5 wt. % more than 1 wt. %, more than 3 wt. %, less than 5 wt. %, or more than 8 wt. % linseed oil.

In some embodiments, an organoleptic composition comprises one or more excipients. For example, organoleptic compositions may include a surfactant. Suitable surfactants may include, but are not limited to, those derived from functionalization of sorbitan. For example, in some embodiments, the organoleptic composition may comprise sorbitan ester surfactants, ethoxylated sorbitan ester surfactants (polysorbates), or any mixtures thereof. It should be recognized that certain classes of surfactants may be especially useful, including for example, sorbitan ester surfactants, ethoxylated sorbitan ester surfactants (polysorbates), or any mixtures thereof, wherein the ester is moiety is oleate. In some embodiments, the organoleptic composition comprises surfactants selected from the group consisting of polyethylene glycol sorbitan monooleate, sorbitan monooleate, sorbitan trioleate, and any combination thereof. An example of a suitable polyethylene glycol sorbitan monooleate is Tween® 80. An example of a suitable sorbitan monooleate is Span® 80. An example of a suitable sorbitan trioleate is Span® 85. In some embodiments, an organoleptic composition may include from 10 to 50 wt. %, from 15 to 40 wt. %, or from 20 to 30 wt. % surfactants. In some embodiments, an organoleptic composition may include less than 50 wt. %, less than 45 wt. %, less than 40 wt. %, less than 35 wt. %, less than 30 wt. %, less than 25 wt. %, less than 20 wt. %, or less than 15 wt. % surfactants. In some embodiments, an organoleptic composition may include more than 10 wt. %, more than 15 wt. %, more than 20 wt. %, more than 25 wt. %, more than 30 wt. %, more than 35 wt. %, more than 40 wt. %, or more than 45 wt. % surfactants.

Another example of an excipient that may be included in an organoleptic composition is a penetration enhancer. Penetration enhancers can enhance drug penetration into the skin through transdermal drug delivery or topical administration. As used herein, a penetration enhancer can help the active ingredient(s) of a topical analgesic gel composition penetrate the skin to provide their intended effect to a user. In some embodiments, the penetration enhancer may include an alkylene glycol. In some embodiments, the penetration enhancer comprises pentylene glycol. In some embodiments, an organoleptic composition may include from 10 to 50 wt. %, from 20 to 45 wt. %, or from 30 to 40 wt. % penetration enhancer. In some embodiments, an organoleptic composition may include more than 10 wt. %, more than 15 wt. %, more than 20 wt. %, more than 25 wt. %, more than 30 wt. %, more than 35 wt. %, more than 40 wt. %, or more than 45 wt. % penetration enhancer. In some embodiments, an organoleptic composition may include less than 50 wt. %, less than 45 wt. %, less than 40 wt. %, less than 35 wt. %, less than 30 wt. %, less than 25 wt. %, less than 20 wt. %, or less than 15 wt. % penetration enhancer.

As described above, the organoleptic composition including sensates, essential oils and linseed oil, and optionally also further excipients, may be incorporated into topical analgesic gel compositions possessing high concentrations of menthol and camphor, including topical analgesic gel compositions of the present disclosure.

Although organoleptic compositions are described herein with specific reference to their use in the topical analgesic gel compositions of the present disclosure, it should be recognized that the organoleptic composition as described herein may be tailored for incorporation into different formulation types also having high concentrations of menthol and camphor, including emulsions, gels, sprays, etc. It should also be recognized that organoleptic compositions as described herein may be adapted to include varied combinations of the cooling and warming sensates, or varied relative concentrations of the sensates to the essential oil mixture, or even exclude certain or all optional excipients.

Additional Ingredients

Topical analgesic gel compositions provided herein may also include ingredients including, but not limited to, a polymeric viscosity builder, a fragrance blend, glycerin, a chelating agent, a neutralizing and/or a solvent. Additionally, topical analgesic gel compositions provided herein do not comprise fats or waxes that are solid at room temperature.

In some embodiments, a topical analgesic gel composition may include one or more polymeric viscosity builders. In particular, a polymeric viscosity builder may help stabilize topical analgesic gel compositions comprising a relatively high payload of menthol and/or camphor provided herein. Suitable polymeric viscosity builders can include carbomers. For example, commercially-available carbomers include those of the Carbopol® family. Carbomers are polymers of acetic acid having a relatively low pH. However, at higher pHs (i.e., around 5.0 or 6.0), they will thicken in solution. Topical analgesic gel compositions comprising too much of a polymeric viscosity builder may result in a formulation that is too thick. This could make application (e.g., from a tube or a roll-on applicator) and spreading on the skin difficult. Conversely, topical analgesic gel compositions comprising too little polymeric viscosity can make the composition too thin, also making application and spreading into the skin difficult. In some embodiments, a topical analgesic gel composition may include from 0.1 to 10 wt. % polymeric viscosity builder, from 0.5 to 5 wt. %, or from 0.5 to 2 wt. % polymeric viscosity builder. In some embodiments, a topical analgesic gel composition may include less than 10 wt. %, less than 5 wt. %, less than 3 wt. %, less than 2 wt. %, less than 1.5 wt. %, less than 1 wt. %, less than 0.8 wt. %, or less than 0.5 wt. % polymeric viscosity builder. In some embodiments, a topical analgesic gel composition may include more than 0.1 wt. %, more than 0.3 wt. %, more than 0.5 wt. %, more than 0.8 wt. %, more than 1 wt. %, more than 1.5 wt. %, more than 2 wt. %, more than 2.5 wt. %, more than 3 wt. %, or more than 5 wt. % polymeric viscosity builder.

In some embodiments, topical analgesic compositions may include a fragrance blend. In some embodiments, a fragrance blend may provide a pleasant fragrance as a mask, and/or to complement the natural scent of menthol and camphor. For example, a fragrance blend may provide a mint effect with soothing qualities and botanical facets. For example, a fragrance blend may include one or more fragrances including, but not limited to, sage, bergamot, spearmint, lemon, rose, jasmine, lavender, cedar wood, amber, musk, and/or eucalyptus. In some embodiments, a topical analgesic composition may include from 0.01 to 10 wt. %, from 0.1 to 5 wt. %, or from 0.5 to 3 wt. % fragrance blend. In some embodiments, a topical analgesic composition includes less than 10 wt. %, less than 8 wt. %, less than 5 wt. %, less than 3 wt. %, less than 1 wt. %, or less than 0.5 wt. % fragrance blend. In some embodiments, the topical analgesic includes more than 0.1 wt. %, more than 0.5 wt. % more than 1 wt. %, more than 3 wt. %, less than 5 wt. %, or more than 8 wt. % fragrance blend.

Topical analgesic gel compositions according to some embodiments provided herein may comprise glycerin. Glycerin is a colorless, odorless, viscous liquid that is commonly used as a sweetener in food products. However, when used in topical analgesic gel compositions disclosed herein, glycerin can moisturize the skin and act as a solubilizer for certain oils. Additionally, topical analgesic gel compositions without glycerin may leave "white" streaks on the skin once the composition has dried (due to the carbomer residue on dried skin). However, colorless glycerin can counteract this white streaking, the exact mechanism being unknown. Topical analgesic gel compositions having too little glycerin may be less moisturizing and may still leave some white streaking. Topical analgesic gel compositions having too much glycerin may be less effective and less pleasing (i.e., having a sticky feel) to the user (including more glycerin in the formulation means including less of other components such as less active ingredient(s), less essential oil blend, less sensates, less fragrance, etc.). In some embodiments, topical analgesic gel compositions may include from 0.1 to 15 wt. %, from 0.5 to 10 wt. %, or from 1 to 5 wt. % glycerin. In some embodiments, topical analgesic gel compositions may include less than 15 wt. %, less than 10 wt. %, less than 5 wt. %, less than 3 wt. %, less than 1 wt. %, or less than 0.5 wt. % glycerin. In some embodiments, topical analgesic gel compositions may include more than 0.1 wt. %, more than 0.5 wt. % glycerin.

In some embodiments, a topical analgesic gel composition may include a chelating agent. Suitable chelating agents include, but are not limited to, salts of ethylenediaminetetraacetic acid (EDTA) such as disodium EDTA, tetrasodium EDTA, calcium sodium EDTA, errous bis-glycinate, pentane-2,4-dione, clathro chelate complexes, methylene phosphonic acid, 1,2-bis (o-amino phenoxy) ethane-N,N,N',N'-tetra acetic acid, cryptands, deferasirox, 2,3-di hydroxy benzoic acid, 2,3-di mercapto-1-propane sulfonic acid, methylene phosphonic acid, 2-hydroxy phenyl acetic acid, ethylene di amine-N,N'-di succinic acid, etidronic acid. In some embodiments, topical analgesic gel compositions may include from 0.01 to 5 wt. %, from 0.05 to 3 wt. %, or from 0.1 to 1 wt. % chelating agent. In some embodiments, a topical analgesic gel composition may include less than 5 wt. %, less than 3 wt. %, less than 2 wt. %, less, than 1.5 wt. %, less than 1 wt. %, less than 0.8 wt. %, less than 0.5 wt. %, less than 0.3 wt. %, less than 0.1 wt. % or less than 0.05 wt. % chelating agent. In some embodiments, a topical analgesic gel composition may include more than 0.01 wt. %, more than 0.05 wt. %, more than 0.1 wt. %, more than 0.3 wt. %, more than 0.5 wt. %, more than 0.8 wt. %, more than 1 wt. %, more than 1.5 wt. %, more than 2 wt. %, or more than 3 wt. % chelating agent.

In some embodiments, a topical analgesic gel composition may include a neutralizing agent. Carbomers, explained in detail above, typically have a relatively low pH (e.g., −3.0). Thus, a neutralizing agent may be used to lower the pH of the composition to a safe level for skin application. Suitable neutralizing agents include, but are not limited to, alkanolamines. An example of a suitable alkanolamine includes aminomethyl propanol. Too little neutralizing agent in a topical analgesic gel composition may not sufficiently neutralize the composition and build viscosity. Too much neutralizing agent may change the pH too much in the opposite direction, may cause viscosity to fall, and may also cause skin irritation due to high pH (e.g., too much neutralizing agent added to an acidic solution may result in a solution that is too basic to safely apply to the skin). In some embodiments, topical analgesic gel compositions may include from 0.01 to 5 wt. %, from 0.05 to 3 wt. %, or from 0.1 to 1 wt. % neutralizing agent. In some embodiments, topical analgesic gel compositions may include less than 5 wt. %, less than 3 wt. %, less than 2 wt. %, less than 1.5 wt. %, less than 1 wt. %, less than 0.8 wt. %, less than 0.5 wt. %, less than 0.3 wt. %, less than 0.1 wt. %, or less than 0.05 wt. % neutralizing agent. In some embodiments, topical analgesic gel compositions may include more than 0.01 wt. %, more than 0.05 wt. %, more than 0.1 wt. %, more than 0.3 wt. %, more than 0.5 wt. %, more than 0.8 wt. %, more than 0.8 wt. %, more than 1 wt. %, more than 1.5 wt. %, more than 2 wt. %, or more than 3 wt. % neutralizing agent.

Topical analgesic gel compositions according to embodiments provided herein may include a solvent. Suitable solvents may include alcohol (e.g., ethanol) and/or water. In some embodiments, menthol and/or camphor, at certain concentrations, may be more soluble in alcohol than in water. Thus, topical analgesic gel compositions provided herein may include at least some alcohol as a solvent. In some embodiments, topical analgesic gel compositions may include both alcohol and purified water. A suitable alcohol may include specially denatured alcohol 40-B 190 proof. In some embodiments, a topical analgesic composition may include from 40 to 90 wt. %, from 50 to 80 wt. %, or from 60 to 70 wt. % solvent. In some embodiments, a topical analgesic composition may include less than 90 wt. %, less than 85 wt. %, less than 80 wt. %, less than 75 wt. %, less than 70 wt. %, less than 65 wt. %, less than 60 wt. %, less than 55 wt. %, less than 50 wt. %, or less than 45 wt. % solvent. In some embodiments, a topical analgesic composition may include more than 40 wt. %, more than 45 wt. %, more than 50 wt. %, more than 55 wt. %, more than 60 wt. %, more than 65 wt. %, more than 70 wt. %, more than 75 wt. %, more than 80 wt. %, or more than 85 wt. % solvent.

As discussed above, topical analgesic gel compositions provided herein may not include any solid fats or waxes. Conventional gels and/or creams often include solid fats or waxes such as soft paraffin, hard paraffin, wool Fat (anhydrous lanolin), beeswax, cholesterol, cetostearyl alcohol, cetyl ester wax, cetylalcohol, glyceryl monostearate, stearic acid, carnauba wax, cetyl palmitate, arachidic acid, cetyl palmitate, cocoa butter, shea butter, microcrystalline wax, candelillia wax, olive butter, lauryl laurate, castor wax, ozokerite wax, polyhydroxy stearic acid, sunflower wax, rice bran wax, jojoba wax, castor wax, and spermaceti. Fats and waxes such as these are all solid at room temperature. However, topical analgesic gel compositions provided herein can achieve a high payload of active ingredients without including a solid fat or wax, such as the solid fats and/or waxes listed above.

Topical Analgesic Gel Compositions Comprising an Organoleptic Composition

Discussed below are topical analgesic gel compositions comprising an organoleptic composition as described above. In particular, the compounds/ingredients described below have been introduced with respect to the organoleptic compositions disclosed above and are reiterated below with respect to the topical analgesic gel composition as a whole. As described in detail above, organoleptic compositions provided herein may be incorporated into topical analgesic gel compositions to add to the sensation of long-lasting pain-relieving effect, to provide a pleasant fragrance as a mask, and/or to complement the natural scent of menthol and camphor. An organoleptic composition according to embodiments provided herein may include cooling and warming sensates, an essential oil mixture, linseed oil, and optionally also further excipients (e.g., vitamin E oil, a surfactant, a penetration enhancer).

In some embodiments, a topical analgesic gel composition may include from 1 to 30 wt. %, from 2 to 20 wt. %, or from 3 to 8 wt. % organoleptic composition. In some embodiments, a topical analgesic gel composition may include more than 1 wt. %, more than 2 wt. %, more than 3 wt. %, more than 5 wt. %, more than 8 wt. %, more than 10 wt. %, more than 15 wt. %, more than 20 wt. %, or more than 25 wt. % organoleptic composition. In some embodiments, a topical analgesic gel composition may include less than 30 wt. %, less than 25 wt. %, less than 20 wt. %, less than 15 wt. %, less than 10 wt. %, less than 8 wt. %, less than 5 wt. %, less than 3 wt. %, or less than 2 wt. % organoleptic composition.

In some embodiments, a topical analgesic gel composition comprising the organoleptic composition provide herein may include one or more sensates including, but not limited to, menthoxypropanediol, isopulegol, and vanillyl butyl ether, and any combination thereof.

As discussed above, menthoxypropanediol is a sensate that can provide a cooling sensation to the skin. In some embodiments, a topical analgesic composition comprising the organoleptic composition provided herein includes from 0.01 to 10 wt. %, from 0.05 to 5 wt. %, or from 0.1 to 1 wt. % menthoxypropanediol. In some embodiments, a topical analgesic composition comprising the organoleptic composition provide herein includes less than 10 wt. %, less than 8 wt. %, less than 5 wt. %, less than 3 wt. %, less than 1 wt. %, less than 0.8 wt. %, less than 0.5 wt. %, less than 0.3 wt. %, less than 0.1 wt. %, or less than 0.05 wt. % menthoxypropanediol. In some embodiments, a topical analgesic composition comprising the organoleptic composition provide herein includes more than 0.01 wt. %, more than 0.05 wt. %, more than 0.1 wt. %, more than 0.3 wt. %, more than 0.5 wt. %, more than 0.8 wt. %, more than 1 wt. %, more than 3 wt. %, less than 5 wt. %, or more than 8 wt. % menthoxypropanediol. An example of a commercially-available menthoxypropanediol is Coolact® 10.

As discussed above, isopulegol is a sensate that can provide a cooling effect on the skin. In some embodiments, a topical analgesic gel composition comprising the organoleptic composition provided herein includes from 0.01 to 10 wt. %, from 0.05 to 5 wt. %, or from 0.1 to 1 wt. % isopulegol. In some embodiments, a topical analgesic gel composition comprising the organoleptic composition provide herein includes less than 10 wt. %, less than 8 wt. %, less than 5 wt. %, less than 3 wt. %, less than 1 wt. %, less than 0.8 wt. %, less than 0.5 wt. %, less than 0.3 wt. %, less than 0.1 wt. %, or less than 0.05 wt. % isopulegol. In some embodiments, a topical analgesic gel composition comprising the organoleptic composition provide herein includes more than 0.01 wt. %, more than 0.05 wt. %, more than 0.1 wt. %, more than 0.3 wt. %, more than 0.5 wt. %, more than 0.8 wt. %, more than 1 wt. %, more than 3 wt. %, less than 5 wt. %, or more than 8 wt. % isopulegol. An example of a commercially-available isopulegol includes Coolact® P.

As described in detail above, vanillyl butyl ether is a sensate that can provide a warming sensation on the skin. In some embodiments, a topical analgesic gel composition comprising the organoleptic composition provided herein includes from 0.001 to 1 wt. %, from 0.005 to 0.5 wt. %, or from 0.01 to 0.1 wt. % vanillyl butyl ether. In some embodiments, a topical analgesic gel composition comprising the organoleptic composition provide herein includes less than 1 wt. %, less than 0.8 wt. %, less than 0.5 wt. %, less than 0.3 wt. %, less than 0.1 wt. %, less than 0.05 wt. %, less than 0.01 wt. %, or less than 0.005 wt. % vanillyl butyl ether. In some embodiments, a topical analgesic gel composition comprising the organoleptic composition provide herein includes more than 0.001 wt. %, more than 0.005 wt. %, more than 0.01 wt. %, more than 0.05 wt. %, more than 0.1 wt. %, more than 0.3 wt. %, more than 0.5 wt. %, or more than 0.8 wt. % vanillyl butyl ether. An example of a commercially-available vanillyl butyl ether is Hotact® VBE.

In some embodiments, a topical analgesic composition comprising the organoleptic composition provided herein includes an essential oil mixture comprising one or more essential oils and/or vitamin E. Essential oils can provide a more pleasant sensory experience for a user by complementing and/or masking the odors of menthol and/or camphor. Vitamin E, when applied to the skin, can be moisturizing and can help protect the skin from free radical damage. In some embodiments, the essential oil mixture can include one or more of peppermint (*Mentha piperita*) oil, eucalyptus (*Eucalyptus globulus*) oil, rosemary (*Rosmarinus officinalis*) oil, clove (*Eugenia caryophyllata*) oil, Spanish marjoram (*Thymus mastichina*) oil and frankincense (*Olibanum* or *Boswellia carterii*) oil, and/or vitamin E. In some embodiments, a topical analgesic composition comprising the organoleptic composition provided herein comprises from 0.01 to 10 wt. %, from 0.05 to 5 wt. %, or from 0.1 to 1 wt. % essential oil mixture. In some embodiments, a topical analgesic composition comprising the organoleptic composition provide herein includes less than 10 wt. %, less than 8 wt. %, less than 5 wt. %, less than 3 wt. %, less than 1 wt. %, less than 0.8 wt. %, less than 0.5 wt. %, less than 0.3 wt. %, less than 0.1 wt. %, or less than 0.05 wt. % essential oil mixture. In some embodiments, the topical analgesic includes more than 0.01 wt. %, more than 0.05 wt. %, more than 0.1 wt. %, more than 0.3 wt. %, more than 0.5 wt. %, more than 0.8 wt. %, more than 1 wt. %, more than 3 wt. %, more than 5 wt. %, or more than 8 wt. % essential oil mixture.

In some embodiments, a topical analgesic gel composition comprising the organoleptic composition provided herein includes linseed oil. A topical analgesic gel composition comprising the organoleptic composition provided herein may include from 0.001 to 5 wt. % or from 0.01 to 1 wt. % linseed oil. In some embodiments, a topical anal-gesic gel composition comprising the organoleptic compo-sition provide herein can include less than 5 wt. %, less than 4 wt. %, less than 3 wt. %, less than 2 wt. %, less than 1 wt. %, less than 0.5 wt. %, less than 0.1 wt. %, less than 0.08 wt. %, less than 0.05 wt. %, less than 0.03 wt. %, or less than 0.01 wt. % linseed oil. In some embodiments, a topical analgesic gel composition comprising the organoleptic com-position provide herein may include more than 0.001 wt. %, more than 0.01 wt. %, more than 0.03 wt. %, more than 0.05 wt. %, more than 0.08 wt. %, more than 0.1 wt. %, more than 0.3 wt. %, more than 0.5 wt. %, more than 0.8 wt. %, more than 1 wt. %, more than 2 wt. %, more than 3 wt. %, or more than 4 wt. % linseed oil.

Applying/Using Topical Analgesic Gel Compositions and Methods of Preparing Topical Analgesic Compositions Provided below is a discussion of various method of applying topical analgesic gel compositions and methods of preparing topical analgesic compositions according to some embodiments provided herein.

Applying/Using Topical Analgesic Gel Compositions

As described above, topical analgesic gel compositions provided herein may be applied using a tube applicator or a roll-on applicator. Conventional cream-like formulations comprising fats or waxes generally cannot be applied using a roll-on applicator because the formulation cracks or agglomerates due to the shear force applied to the formu-lation as it is forced out of the applicator (i.e., between the roller ball and a side of the container). Further, conventional cream-like formulations are not easily spreadable into the skin. However, because topical analgesic gel compositions provided herein do not include fats or waxes and are light, they may be prepared in a roll-on applicator for use.

Additionally, topical analgesic gel compositions provided herein may also be packaged in a tube applicator for use. Because topical analgesic gel compositions have a light, emulsified gel (or emulgel) consistency, they are not too thick, nor too thin, to be packaged in a tube applicator and easily expelled from the tube applicator and rubbed in to the skin by a user.

To be compatible with a roll-on and/or a tube applicator, achieving a particular viscosity is beneficial. If the viscosity is too high, the topical analgesic gel composition may be difficult to expel from the applicator and difficult to rub in to the skin. If the viscosity is too low, the topical analgesic gel composition may spill out of the applicator and be difficult to apply to a desired area of the skin without having the topical analgesic composition spread to other areas (both on the skin and elsewhere). In some embodiments, the viscosity of the topical analgesic gel composition may be from 10,000 to 200,000 centipoise (cps), from 25,000 to 150,000 cps, or from 60,000 to 110,000 cps. In some embodiments, the viscosity of the topical analgesic gel composition may be less than 200,000 cps, less than 175,000 cps, less than 150,000 cps, less than 125,000 cps, less than 100,000 cps, less than 110,000 cps, less than 75,000 cps, less than 50,000 cps, or less than 25,000 cps. In some embodiments, the viscosity of the topical analgesic gel, cream, or paste com-position may be more than 10,000 cps, more than 25,000 cps, more than 50,000 cps, more than 75,000 cps, more than 100,000 cps, more than 110,000 cps, more than 125,000 cps, more than 150,000 cps, or more than 175,000 cps.

Other beneficial properties of the topical analgesic gel composition include specific gravity and pH. In some embodiments, the specific gravity of the topical analgesic composition may be from 0.2 to 2.0, from 0.4 to 1.5, or from 0.6 to 1.2. In some embodiments, the specific gravity may be greater than 0.2, greater than 0.4, greater than 0.6, greater than 0.8, greater than 1.0, greater than 1.2, greater than 1.4, or greater than 1.6. In some embodiments, the specific gravity may be less than 2.0, less than 1.8, less than 1.6, less than 1.4, less than 1.2, less than 1.0, less than 0.8, less than 0.6, or less than 0.4.

In some embodiments, the pH may be from 4.0 to 9.0, from 4.5 to 8.5, or from 5.0 to 6.0. In some embodiments, the pH may be greater than 4.0, greater than 4.5, greater than 5.0, greater than 5.5, greater than 6.0, greater than 6.5, greater than 7.0, or greater than 7.5. In some embodiments, the pH may be less than 9.0, less than 8.5, less than 8.0, less than 7.5, less than 7.0, less than 6.5, less than 6.0, less than 5.5, or less than 5.0.

Methods of Preparing Topical Analgesic Compositions

Provided herein are methods of preparing topical analge-sic gel compositions according to embodiments provided herein.

In some embodiments, a menthol/camphor melt can be prepared. In particular, the menthol and/or camphor can be heated in a water bath at a temperature from 30 to 50° C. or from 35 to 45° C. In some embodiments, the temperature may be more than 30° C., more than 35° C., or more than 40° C. In some embodiments, the temperature may be less than 50° C., less than 45° C., or less than 40° C. The menthol and/or camphor may be heated until melted into a colorless liquid, at which time the melt may be removed from the heat and let cool to room temperature.

In some embodiments, camphor may be dissolved in room temperature alcohol. The camphor and alcohol may be combined in a side-phase vessel. The menthol may be added to the camphor solution. In some embodiments, the menthol may be added to the camphor and alcohol solution such that $T_{m,\ menthol} < T_{addition} \leq 40°$ C. The menthol, camphor, alcohol solution may then be added to a main batch vessel.

In some embodiments, camphor may be dissolved in room temperature alcohol. The camphor and alcohol may be combined in a side-phase vessel. The menthol may be held at $T_{m,\ menthol} < T_{addition} \leq 40°$ C. In some embodiments, the menthol and camphor solution may be added to a main batch vessel separately.

In some embodiments, an aqueous dispersion may be prepared. The aqueous dispersion may include weighing and transferring several components into a mixer. For example, the following components may be weighed and transferred to the mixer: purified water, histamine dihydrochloride, carbomer, disodium EDTA, and glycerin. In some embodi-ments, these components may be transferred into the mixer in the order listed. The lid of the mixer may be put in place with the homogenizer shaft installed.

In some embodiments, several additional components may be weighed and placed in an appropriately-sized con-tainer (e.g., beaker, SS pot). For example, the following components may be introduced: polysorbate 80, sorbitan monooleate, pentylene glycol, vanillyl butyl ether, men-thoxypropanediol, isopulegol, linseed oil, vitamin E, essen-tial oil blend, fragrance blend, and/or the menthol-camphor melt prepared above.

In some embodiments, the total amount of alcohol may be weighed in an appropriately-sized container. In some embodiments, a portion of the total alcohol may be trans-ferred into the original container used to prepare the men-thol-camphor melt. For example, about ¼, about ½, or about ¾ of the alcohol may be transferred into the original container used to prepare the menthol-camphor melt. This portion of ethanol may be mixed or agitated with, for example, an overhead mixer or spatula until a uniform mixture is achieved. In some embodiments, this portion of the alcohol (and residual menthol-camphor melt) may be transferred into the container comprising polysorbate 80, sorbitan monooleate, pentylene glycol, vanillyl butyl ether, menthoxypropanediol, isopulegol, linseed oil, vitamin E, essential oil blend, fragrance blend, and/or the menthol-camphor melt prepared above.

In some embodiments, the IKA mixer may be operated to mix the purified water, histamine dihydrochloride, carbomer, disodium EDTA, and glycerin. These components may be mixed using a suitable mixer. For example, a suitable mixer may include those provided by IKA Laboratory Equipment. Using side sweeps and/or a homogenizer, the histamine dihydrochloride, carbomer, disodium EDTA, and glycerin may dissolute into the solvent. In some embodiments, the mixer may be used with both side sweep and the homogenizer. In some embodiments, the mixer may mix from 1 to 60 minutes. In some embodiments, the mixer may mix for less than 60 minutes, less than 45 minutes, less than 30 minutes, less than 20 minutes, less than 15 minutes, less than 10 minutes, less than 5 minutes, or less than 3 minutes. In some embodiments, the mixer may mix for more than 1 minute, more than 3 minutes, more than 5 minutes, more than 10 minutes, more than 15 minutes, more than 20 minutes, more than 30 minutes, or more than 45 minutes.

In some embodiments, the polysorbate 80, sorbitan monooleate, pentylene glycol, vanillyl butyl ether, menthoxypropanediol, isopulegol, linseed oil, vitamin E, essential oil blend, fragrance blend, and/or the menthol-camphor melt and the portion of ethanol comprising residual menthol-camphor melt may be added to the mixer. In some embodiments, the mixer may be used with both side sweep and the homogenizer. In some embodiments, the mixer may mix from 1 to 60 minutes. In some embodiments, the mixer may mix for less than 60 minutes, less than 45 minutes, less than 30 minutes, less than 20 minutes, less than 15 minutes, less than 10 minutes, less than 5 minutes, or less than 3 minutes. In some embodiments, the mixer may mix for more than 1 minute, more than 3 minutes, more than 5 minutes, more than 10 minutes, more than 15 minutes, more than 20 minutes, more than 30 minutes, or more than 45 minutes.

In some embodiments, the remaining alcohol may be transferred to the container that was holding the polysorbate 80, sorbitan monooleate, pentylene glycol, vanillyl butyl ether, menthoxypropanediol, isopulegol, linseed oil, vitamin E, essential oil blend, fragrance blend, and/or the menthol-camphor melt and the portion of ethanol comprising residual menthol-camphor melt and mixed with any residual materials remaining in the container. For example, the solution may be mixed with an overhead mixer or spatula until a uniform mixture is achieved. This solution may then be transferred to the mixer. In some embodiments, the materials in the mixer may be mixed and homogenized until a uniform dispersion is achieved. In some embodiments, once a uniform dispersion is achieved, the mixer may continue mixing with side sweeps.

In some embodiments, aminomethyl propanol may be added to the mixer and mixed until gelation occurs and a uniform mixture is achieved Once uniform, the solution may be removed from the mixer and placed into an appropriate balance. Solvent (e.g., purified water) may be used to QS the mixture if necessary. The mixture may be added to an appropriate air-tight container.

Process parameters that may be optimized during the various mixing steps can include mix speed of side sweeps and mix speed of homogenizer.

In some embodiments, the mix speed of the side sweeps may be constant during the mixing process. In some embodiments, the mix speed of the side sweeps may vary during the mixing process. In some embodiments, the mix speed of side sweeps may be from 30 to 300 rpm, from 40 to 200 rpm, or from 50 to 150 rpm. In some embodiments, the mix speed of side sweeps may increase one or more times during the mixing time. In some embodiments, the mix speed of side sweeps may decrease one or more times during the mixing time. In some embodiments, the homogenizer may be on for all or part of the mixing speed time. In some embodiments, the mix speed of the homogenizer may be from 5000 to 20,000 rpm, from 8000 to 18,000 rpm, or from 10,000 to 15,000 rpm.

EXAMPLES

Example 1: Provided below in Table 2 is an example of a topical analgesic composition according to some embodiments provided herein.

TABLE 2

| Example topical analgesic gel composition. | | |
| --- | --- | --- |
| Ingredient | International Nomenclature of Cosmetic Ingredient Name | Weight percent |
| Menthol USP | Menthol | 15.967 |
| Racemic Camphor USP | Camphor | 5.500 |
| Tween ® 80 | Polysorbate 80 | 1.000 |
| Span ® 80 | Sorbitan Monooleate | 0.500 |
| Carbomer Interpolymer Type A (i.e., Carbopol ® Ultrez 10) | Carbomer | 1.000 |
| Glycerin | Glycerin | 3.000 |
| Hydrolite ® 5 | Pentylene Glycol | 2.000 |
| HOTACT ® VBE | Vanillyl butyl ether | 0.050 |
| Coolact ® 10 | Menthoxypropanediol | 0.630 |
| Coolact ® P | Isopulegol | 0.500 |
| Linseed Oil | Linseed Oil | 0.050 |
| Vitamin E | Vitamin E | 0.500 |
| Essential Oil blend | Peppermint Oil, Eucalyptus Oil, Rosemary Oil, Spanish Marjoram Oil, Clove Oil, Frankincense, Vitamin E | 0.500 |
| Fragrance | Mystic Sage and Minerals | 0.750 |
| Edetate Disodium | Disodium EDTA | 0.500 |
| Aminomethyl Propanol | Aminomethyl Propanol | 0.350 |
| Specially Denatured Alcohol 40-B 190 Proof | Ethanol | 22.000 |
| Purified Water | Purified Water | 45.203 |

Figure 2:
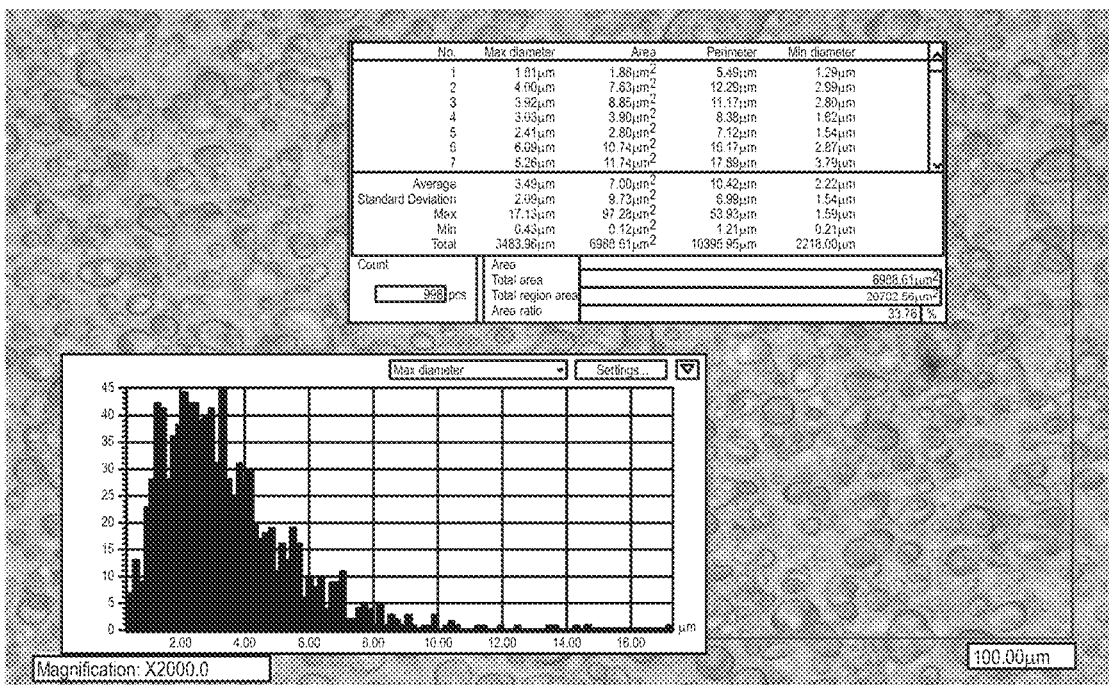
FIG. 2 provides droplet size data of a topical analgesic gel composition, according to some embodiments.

As shown in FIG. 2, the amount of menthol included in the topical analgesic gel composition is just shy of 16 wt. %. Menthol, as an active pharmaceutical ingredient (API), can be used at up to 16 wt. %, which is the maximum allowed concentration as a monograph. However, the total quantity of menthol to be added as an API must be adjusted to account for the menthol contributed by essential oils. As shown in Table 3 below, menthol is an ingredient in peppermint essential oil. In the example provided in Table 3 below, peppermint oil is present in the blend as 14.5 wt. %, and it includes an average of 46.0 wt. % menthol. The total essential oil blend present in the final formula is 0.5 wt. %, as shown in the last column of Table 3. Hence, the amount of menthol contributed from peppermint oil is 46.0 wt. % of 14.5 wt. % of 0.5 wt. %, which is 0.033 wt. %. This amount of menthol contributed by peppermint essential oil can be subtracted from the desired amount of total menthol in the topical analgesic gel composition (e.g., 16 wt. %). Thus, the adjusted additional menthol that can be added to the topical analgesic gel composition is 16 wt. %–0.033 wt. %=15.967 wt. %.

TABLE 3

Accounting for the amount of menthol contributed to the topical analgesic gel composition by the essential oils.

| Composition of Essential Oils Blend | wt. % in essential oil blend | Avg. Menthol Content in individual oil, wt. % | Concentration of EO Blend in total formula, wt. % |
|---|---|---|---|
| Peppermint Oil, Indian or Mentha Piperita (Peppermint) Oil | 14.5 | 46.0 | 0.5 |
| Olibanum or Boswellia Carterii Oil | 10.0 | 0 | |
| Eucalyptus 80/85 or Eucalyptus Globulus Leaf Oil | 14.5 | 0 | |
| Marjoram Oil, Spanish or Thymus Mastichina Flower Oil | 24.5 | | |
| Clove Bud Oil or Eugenia Caryophyllus (Clove) Oil | 10.0 | 0 | |
| Rosemary Spanish or Rosmarinus Officinalis (Rosemary) Leaf Oil | 24.5 | 0 | |
| Vitamin E | 2.0 | 0 | |

Example 2: Provided below is an example of a method of preparing a topical analgesic gel composition according to some embodiments provided herein.

A menthol-camphor melt was prepared by weighing and transferring the menthol and camphor into a sealed vessel. The mixture was heated in a water bath at 40° C. until a uniform colorless liquid was achieved. The mixture was removed from heat and set aside.

An aqueous dispersion was prepared by weighing and transferring the following components in the order listed: purified water, histamine dihydrochloride, carbomer, disodium edetate, and glycerin to an IKA mixer. The IKA mixer lid was placed on the mixer with the homogenizer shaft installed.

In an appropriately-sized container (e.g., beaker or SS pot), the following materials were added in the order provided: Tween® 80, Span® 80, Hydrolite® 5, Hotact® VBE, Coolact® 10, Coolact® P, linseed oil, vitamin E, essential oil blend, fragrance blend, and menthol-camphor melt.

The alcohol was weighed separately. Half of the weighed ethanol was transferred to the original container used to prepare and/or hold the menthol-camphor melt. This portion of the ethanol was agitated or stirred with an overhead mixer/spatula until a uniform mixture was achieved. This uniform mixture comprising alcohol and residual menthol and camphor was transferred to the container comprising Tween® 80, Span® 80, Hydrolite® 5, Hotact® VBE, Coolact® 10, Coolact® P, linseed oil, vitamin E, essential oil blend, fragrance blend, and menthol-camphor melt.

The mixer comprising purified water, histamine dihydrochloride, carbomer, disodium edetate, and glycerin was run with side sweeps and IKA T25 homogenizer until a uniform dispersion was achieved. Note that some foaming may have occurred. Specifically, the mixture was mixed with side sweeps at 75 rpm and the homogenizer at 9000 rpm for a total of 5 minutes. After this 5 minutes of mixing time, the mixture comprising Tween® 80, Span® 80, Hydrolite® 5, Hotact® VBE, Coolact® 10, Coolact® P, linseed oil, vitamin E, essential oil blend, fragrance blend, menthol-camphor melt, and the half portion of ethanol mixed with the residual menthol and ethanol was added to the mixture and the mixture was mixed with side sweeps at 90 rpm for 6 minutes.

The remaining alcohol was added to the container that was holding the Tween® 80, Span® 80, Hydrolite® 5, Hotact® VBE, Coolact® 10, Coolact® P, linseed oil, vitamin E, essential oil blend, fragrance blend, menthol-camphor melt, and the half portion of ethanol mixed with the residual menthol and ethanol and stirred with an overhead mixer or spatula until a uniform mixture was achieved. This mixture was transferred to the mixer. The mixture was mixed with the homogenizer at 13,000 rpm for 5 minutes. Once a uniform dispersion was achieved, the mixer continued to mix with side sweeps for another 1 minute.

Aminomethyl propanol was added to the mixer and mixed with side sweeps at 90 rpm for 10 minutes until gelation took place and a uniform mixture was achieved.

The mixture was removed from the mixer and placed on a balance. Water was used to QS to reach the target batch size and mixed if necessary. The mixture was transferred to an appropriate air tight container for storage.

Example 3: A topical analgesic gel composition according to embodiments provided herein was microscopically analyzed to characterize the gel composition. In particular, FIG. 1 shows an image of a topical analgesic gel composition magnified 2000×. The figure shows that the active ingredients (e.g., menthol, camphor), the sensates, and the essential oils form small droplets within the topical analgesic gel composition. These micron-sized droplets are emulsified/stabilized in the hydro-alcoholic cream base, and the micron-sized droplets do not coalesce or break. This micro-emulsion comprising the small droplets of actives, essential oils, and sensates can lead to faster absorption to skin than a composition having larger droplets. Faster absorption into the skin can lead to rapid action and easier spreadibility. Small droplet sizes can also enhance the stability of the topical analgesic gel composition, leading to an increased shelf life. Additionally, the small droplet size lends itself to a less greasy formulation that disappears faster without being rubbed off on clothing or other parts of the body during application. The small droplet size also provides packaging options. Topical analgesic gel compositions provided herein can be packaged in roll-on application or a tube due to the small droplet size.

FIG. 2 shows a droplet size analysis of the magnified topical analgesic gel composition. As shown in the figure, the average droplet size is 2.22 microns, the maximum droplet size is 10.59 microns, and the minimum droplet size is 0.21 microns. There are extremely small droplet sizes in the lower side of the micron range. As size ranges confirm, this topical analgesic gel composition can be characterized as a stable micro-emulsion cream. The micro-emulsion is essentially the actives, essential oils, and the sensates emulsified by surfactants (e.g., Tween 80 and Span 80) and stabilized by a visocity builder (e.g., carbomer). This micro-emulsion cream is achievable under normal processing conditions without the use of a heated system or specialized high-shear equipment, since the composition does not include any fats and waxes that are solid at room temperature, which are typical constituents of a cream. As described above, the observed droplet sizes are on the small side of the micron range. This small droplet size is only possible due to lack of hard fats and waxes (i.e., fats and waxes that are solid at room temperature), which tend to coalesce and form bigger droplets which float to the top and can destabilize the cream over a period of time. For example, hard fats and waxes typically coalesce and form droplets in the hundreds of microns.

FIGS. 1 and 2 were captured using a VHX 5000 digital microscope (Keyence Corp. America, NJ, USA) and Version 1.4 of the corresponding software. The image was captured by taking a neat sample of a topical analgesic formulation and spreading it thinly on a glass slide. The glass slide with the spread sample was placed under the microscope in light transmittance mode with a magnification factor of 2000×. The image was then digitally analyzed using an automatic area extraction algorithm based upon pixel density.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X".

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A topical analgesic composition comprising:
10 to 20 wt. % menthol, and
4 to 8 wt. % camphor,
wherein the topical analgesic composition comprises droplets having an average droplet size of 0.1 to 5 microns;
wherein the topical analgesic composition is formed by a process comprising forming an eutectic mixture comprising menthol and camphor;
wherein the topical analgesic composition does not comprise a fat or a wax that is solid at room temperature; and
wherein the topical analgesic composition has a viscosity from 60,000 to 110,000 centipoise.

2. The composition of claim 1, wherein the combined amount of menthol and camphor comprises 20 to 25 wt. %.

3. The composition of claim 1, wherein the topical analgesic composition has a pH of 5 to 5.5.

4. The composition of claim 1, wherein the topical analgesic composition has a specific gravity of 0.9 to 1.0.

5. The composition of claim 1, further comprising 0.5 to 1.5 wt. % sensate.

6. The composition of claim 5, wherein the sensate comprises one or more of menthoxypropanediol, isopulegol and vanillyl butyl ether.

7. The composition of claim 1, further comprising 0.1 to 1 wt. % of one or more essential oils.

8. The composition of claim 7, wherein the one or more essential oils comprises one or more of peppermint oil, *eucalyptus* oil, rosemary oil, clove oil, Spanish marjoram oil, and frankincense oil.

9. The composition of claim 1, further comprising 0.1 to 1 wt. % neutralizing agent.

10. The composition of claim 1, further comprising 1 to 3 wt. % one or more surfactants.

11. The composition of claim 1, further comprising 1 to 5 wt. % glycerin.

12. The composition of claim 1, further comprising 1 to 3 wt. % penetration enhancer.

13. The composition of claim 1, wherein the topical analgesic composition is configured to be stored in a tube container.

14. A method for treating muscle and joint ache or pain, comprising administering to a patient in need thereof a topical analgesic composition according to claim 1.

15. A topical analgesic product comprising:
a tube applicator; and
a topical analgesic composition comprising:
10 to 20 wt. % menthol; and
4 to 8 wt. % camphor; and
wherein the topical analgesic composition is formed by a process comprising forming an eutectic mixture comprising menthol and camphor;
wherein the topical analgesic composition does not comprise a fat or a wax that is solid at room temperature;
wherein the topical analgesic composition has a viscosity from 60,000 to 110,000 centipoise;
wherein the topical analgesic composition comprises droplets having an average droplet size of 0.1 to 5 microns; and
wherein the topical analgesic composition is contained within the tube applicator to form the topical analgesic product.

* * * * *